United States Patent [19]
Heckele et al.

[11] Patent Number: 5,846,181
[45] Date of Patent: Dec. 8, 1998

[54] ENDOSCOPIC INSTRUMENT

[75] Inventors: Helmut Heckele, Knittlingen; Uwe Schaumann, Villingen-Schwenningen; Martin Seebach, Oberderdingen, all of Germany

[73] Assignee: Richard Wolf GmbH, Knittlingen, Germany

[21] Appl. No.: 735,897

[22] Filed: Oct. 23, 1996

[30] Foreign Application Priority Data

Nov. 2, 1995 [DE] Germany .................. 195 40 731.8

[51] Int. Cl.$^6$ ....................................... A61B 1/00
[52] U.S. Cl. .................... 600/104; 600/114; 606/144
[58] Field of Search .................. 600/101, 104, 600/114; 606/144, 148, 170, 171

[56] References Cited

U.S. PATENT DOCUMENTS

| | | | |
|---|---|---|---|
| 3,844,272 | 10/1974 | Banko | 606/170 X |
| 4,195,624 | 4/1980 | Douglas | 600/114 |
| 4,773,394 | 9/1988 | Reichstein et al. | 600/114 |
| 5,234,444 | 8/1993 | Christoudias . | |
| 5,336,231 | 8/1994 | Adair . | |
| 5,431,666 | 7/1995 | Sauer et al. | 600/144 X |

FOREIGN PATENT DOCUMENTS 3343867   6/1985   Germany .

*Primary Examiner*—Beverly M. Flanagan
*Attorney, Agent, or Firm*—Cohen, Pontani, Lieberman & Pavane

[57] ABSTRACT

The endoscopic instrument for introducing elongate medical assisting devices into the body of a patient comprises an elongate shank which is provided at its proximal end with a handle for the instrument, whereby the shank comprises at least one recess for receiving and guiding an elongate assisting device, said recess beginning distally and extending at least partly along said shank's length. For improving the introduction of the assisting device into the body of the patient the shank is surrounded by a hollow outer shank which comprises at least one longitudinal slit extending from its distal end along at least a part length of the outer shank, whereby the outer shank is twistable or distally displaceable over the inner shank for overlapping the recess of said inner shank, and can be positioned in the overlapping position.

11 Claims, 4 Drawing Sheets

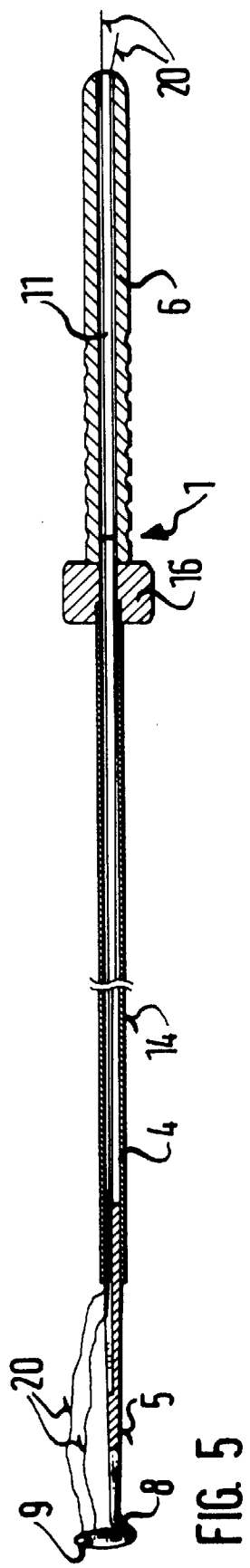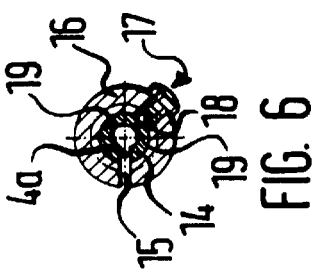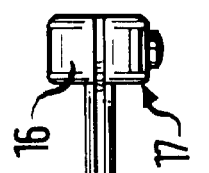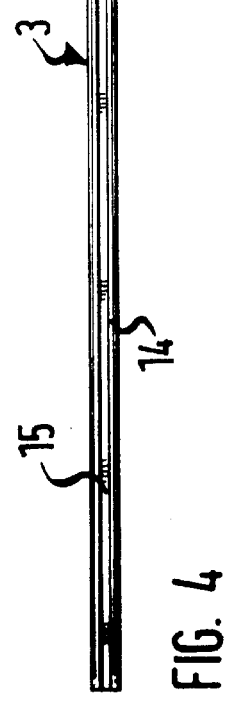

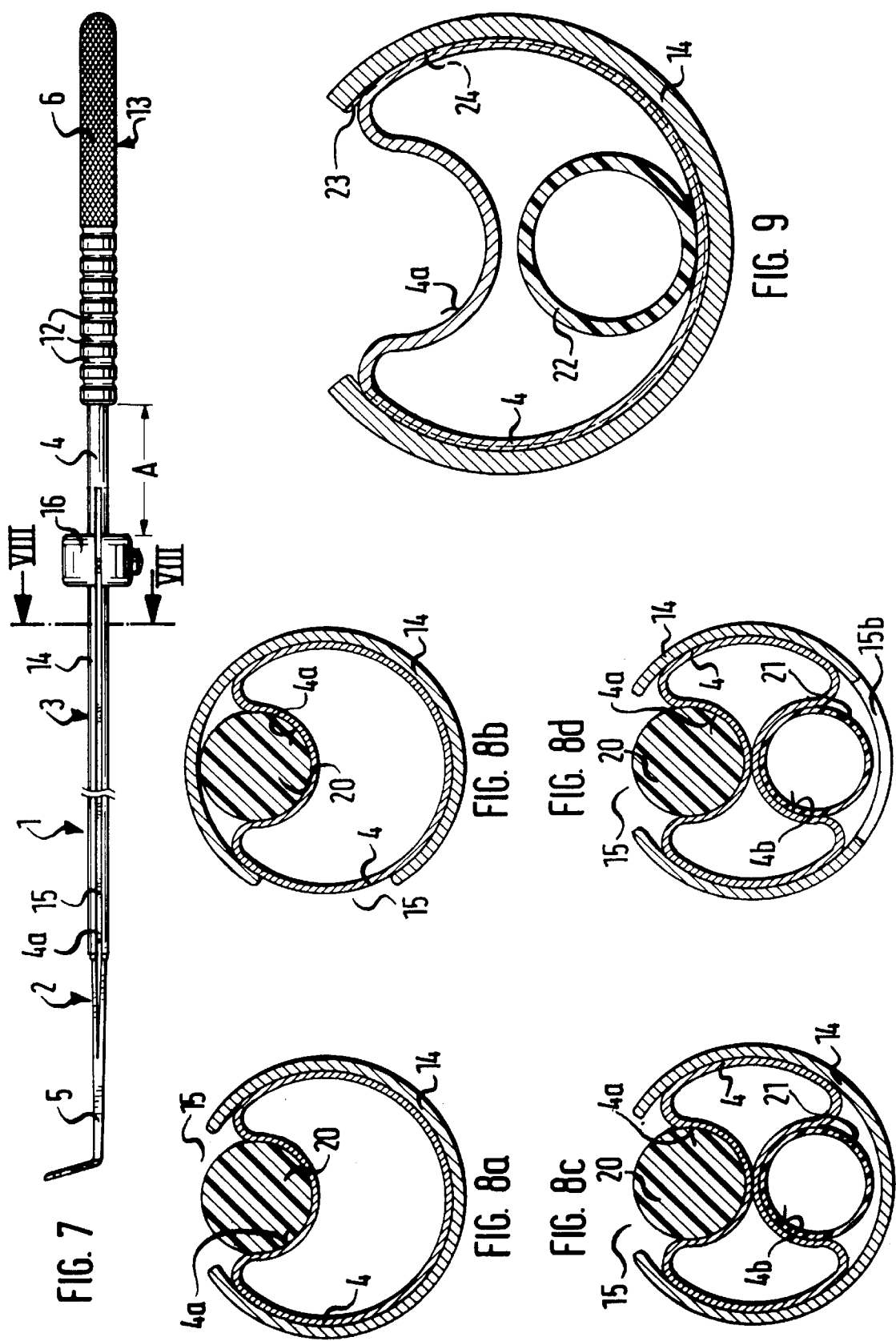

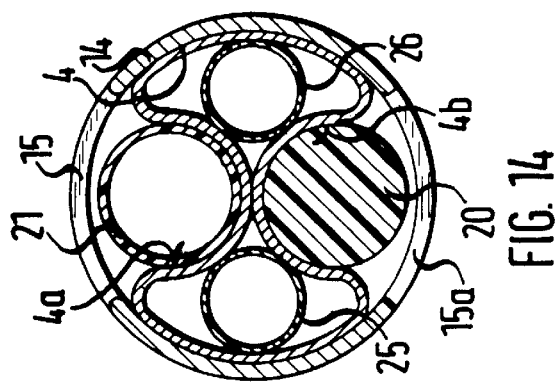
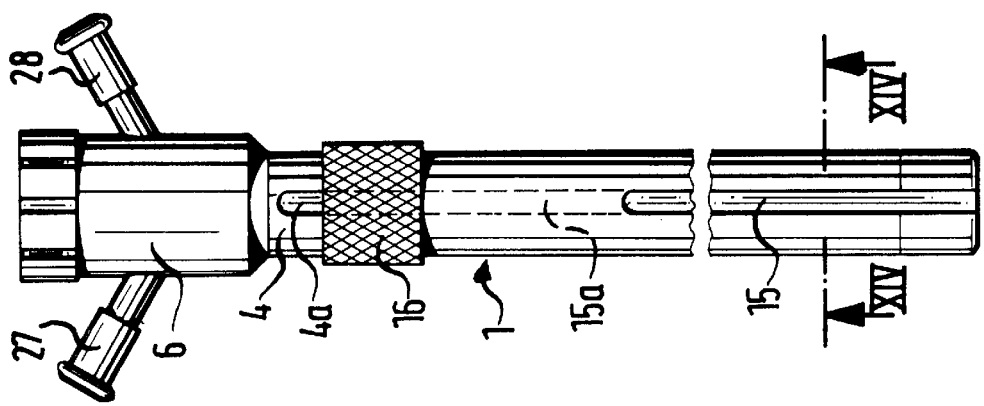
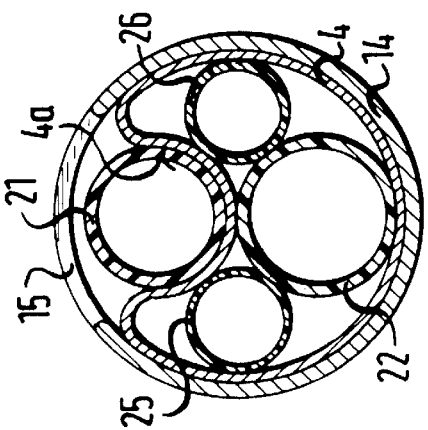
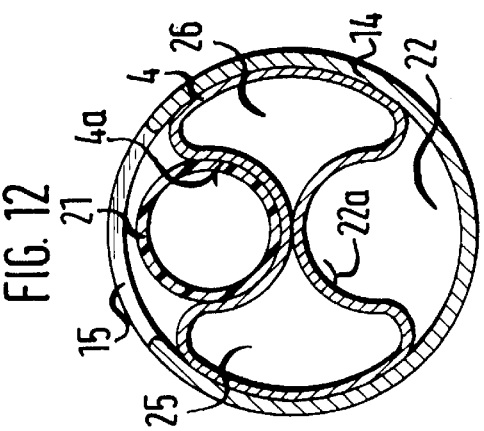
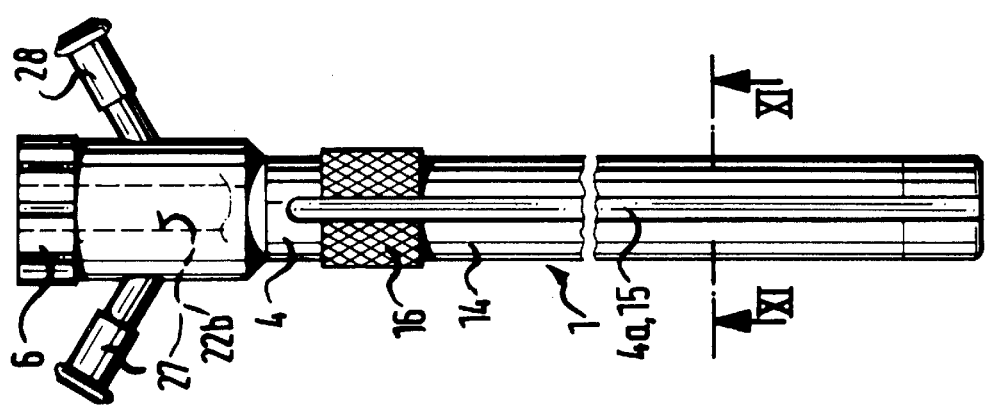

ENDOSCOPIC INSTRUMENT

BACKGROUND OF THE INVENTION

The invention proceeds from an endoscopic instrument according to the preamble of patent claim 1.

DESCRIPTION OF THE PRIOR ART

An endoscopic instrument of this type in the form of a ligaturing instrument is described in DE-A-3504202. This instrument comprises a hollow shank, to the distal end of which is releasably arranged an arcuate needle type threading piece for a ligature thread, and at the proximal end of this hollow shank there is provided a handle. The hollow shank comprises a continuous longitudinal slit which is distally formed with a broadened opening. A locking body for the ligature thread may be applied through this opening. Whilst the ligament thread at the distal side is inserted into the threading piece, in the proximal direction the ligature thread is inserted through the slit of the hollow shank into this shank. With the help of a trocar the ligature instrument together with the ligature thread inserted therein is guided towards the location in the body of the patient to be treated. Although the ligature thread with this instrument is located protected in the hollow shaft during the introduction of the instrument into the body cavity of the patient, there is however the danger that the ligature thread becomes dislocated out of the slit of the hollow shank, which with the practical use of the ligature thread may lead to the entangling of the thread in the body region concerned and thus to unnecessary stress for the patient and complications.

In DE-C-2300840 another ligature instrument is disclosed. This instrument comprises a hollow inner shank with a handle at right angles to this shank at its proximal end, an operating element in the form of a tube surrounding the inner shank and a tube pair running through the inner shank. This tube pair extends distally from the inner shank with a straight section and ends in a distal roughly annular formation. The tube surrounding the inner shank of this known ligature instrument extends in the tube's initial position from the handle up to roughly the annular formation which it maintains closed, this being due to the expanding spring force of the handle. The ends of the tube pair embodying the annular formation expand radially outwards on account of their immanent pretensioning when the operating element is pulled back. The tube pair itself forms a continuous forward and rearward running guiding lumen for the ligature thread. This ligature instrument has proven to be awkward in practical handling, i.e. on introducing the ligature thread into this instrument, since in particular the ligature thread must be threaded into the one tube part of the tube pair with the help of an additional assisting instrument and then pulled back through the other tube part, in order to provide threading material in the annular fomation.

Furthermore, binding and ligature needles are generally known which are comprised of a handle and a needle part in one piece. Distally, the needle part has a desired arch shaped formation which is generally sickle shaped or semicircular and essentially runs bent at right angles to the longitudinal extension of the remaining needle. The distal end of the formation has an eye of a needle for receiving and guiding a ligature thread. The endoscopic work must be carried out very carefully since the inadequate guiding of the ligature thread leads to those previously mentioned entanglements and the related dangers, this lengthening the endoscopic operation and stressing the patient.

SUMMARY OF THE INVENTION

It is the object of the invention to improve the previously cited endoscopic instruments and which, while remaining simple in its construction, ensures a fast and simple insertion of at least one elongate medical assisting device into the instrument, prevents the undesired dislocation of the assisting device out of this instrument and also permits a secure handling of the assisting device in the body of the patient and a careful treatment of the patient.

The solution to this problem is given in patent claim 1.

This solution allows a quick and simple insertion of an assisting device, e.g. a ligature thread or catheter, into the instrument, since for this only a slight twisting of the hollow outer shank to bring its longitudinal slit to overlap with the longitudinally running recess of the inner shank needs to be made, so that the assisting device may be inserted into the recess without any difficulty. By way of a subsequent slight twisting and positioning of the outer shank, the recess of the inner shank is securely occluded so that the assisting device may not dislocate out of the recess. The assisting device is then securely located in the instrument and may be guided towards the location to be operated in the body of the patient and safely operated here without complications for the patient. The operation of the endoscopic instrument according to the invention is likewise simple since to insert an assisting device, the hollow outer shaft needs only to be adjusted by a slight twisting. Moreover the construction of the instrument as a whole remains simple so that it may be produced with relatively low manufacturing costs.

In one design of the endoscopic instrument according to the invention, the outer shank beginning from the distal end of the instrument, extends at least over a part length of the inner shank and the recess of the inner shank projects proximally from the outer shank. In this way a flexible assisting device, e.g. a catheter, may laterally enter the instrument just behind the outer shank, but reasonably far in front of the handle.

In a further design the inner shank is composed of a tube material with at least one longitudinally running recess formed in the tube wall. If for example two recesses are formed then for instance a ligature thread may be inserted into the one recess and a catheter inserted into the other.

In yet a further design, the inner shank in its form as a hollow shank, comprises at least one additional lumen for leading through an additional assisting device, e.g. an endoscope optic. In this way the operating location in the body of the patient may be inspected without using a separate optical endoscope which necessitates a second puncturing of the patient, this being thereby done away with.

Furthermore the outer shank and the inner shank may be separable from one another. In this way both parts may easily be individually cleaned and disinfected after use.

In another design of the endoscopic instrument according to the invention, the hollow outer shank, at its proximal end, is provided with a slotted adjusting ring which is rigidly attached to said outer shank. The adjusting ring comprises a latching device for fixing the outer shank to the inner shank at least in one position in which the recess of the inner shank is overlapped by the outer shank. In this way a simply constructed and operated adjusting device is produced.

In yet a further design of the instrument the handle of the inner shank comprises an elongate component flush with this shank, said component having a receiving groove for the ligature thread, said receiving groove extending in the longitudinal direction of the handle and being flush with the recess of the inner shank. The design of a receiving groove in the handle allows an easy insertion of the ligature thread into the recess or into the hollow space of the inner shank when the outer shank reaches as far as the handle.

BRIEF DESCRIPTION OF THE DRAWINGS

The invention is hereinafter described in more detail by way of the attached drawings. These show:

FIG. 4 a lateral view of a second constructional unit of the embodiment example, FIG. 5 an axial longitudinal section through the embodiment example according to FIG. 1, FIG. 6 a sectional representation taken along line VI—VI in FIG. 1, FIG. 7 the embodiment example in a modified form, FIGS. 8a to 8d an enlarged scale sectional representation taken along line VIII—VIII in FIG. 7, FIG. 9 a further development of the embodiment form acccording to FIG. 8a, FIG. 10 a view of a second embodiment example, FIG. 11 an enlarged scale sectional representation taken along line XI—XI in FIG. 10, FIG. 12 an embodiment example modified with respect to that of FIG. 11, FIG. 13 a view of a third embodiment example, FIG. 14 an enlarged scale sectional representation taken along line XIV—XIV in FIG. 13.

DETAILED DESCRIPTION OF PREFERRED EMBODIMENTS

Figure 1:
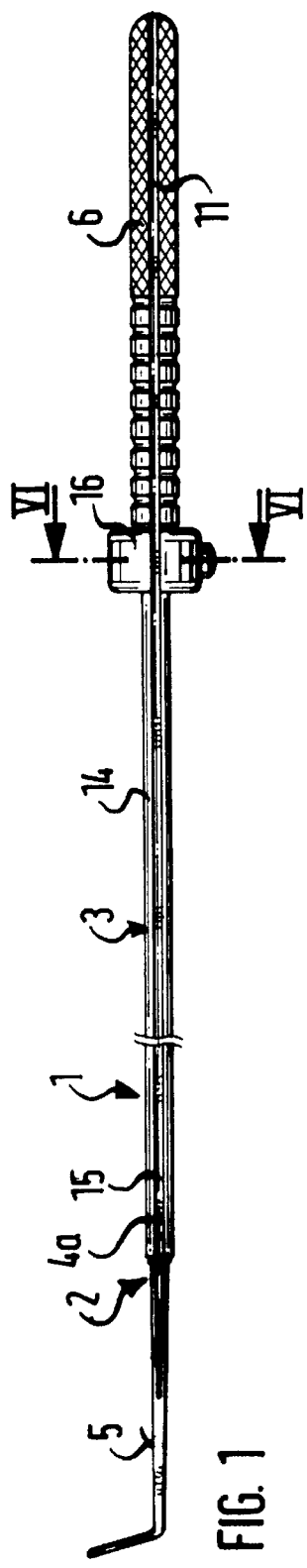
FIG. 1 a lateral view of a first emdodiment example.

The instrument indicated generally at 1, e.g a ligature instrument comprises according to FIG. 1 a first constructional unit 2 as a thread receiver and a second constructional unit 3 which surrounds the first constructional unit and is in the form of a hollow outer shank for securing a ligature thread inserted into the thread receiver 2. The outer shank surrounds the thread receiver coaxially and in the case shown over its whole length.

Figure 2:
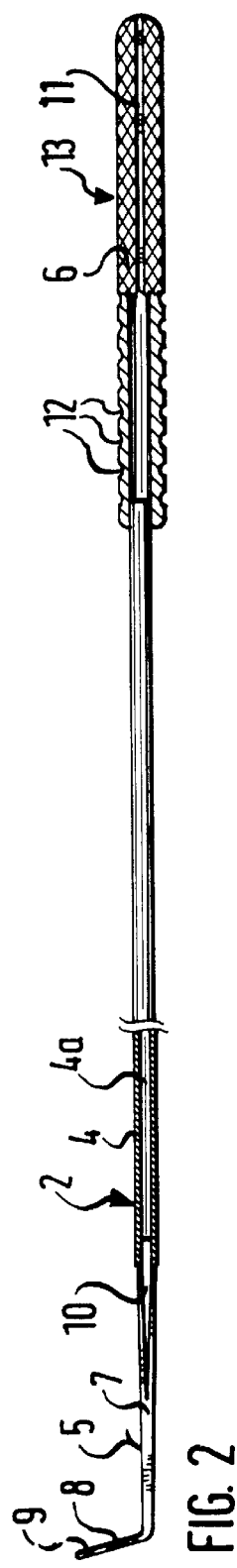
FIG. 2 a lateral view of a first constructional unit of the embodiment example.
Figure 3:
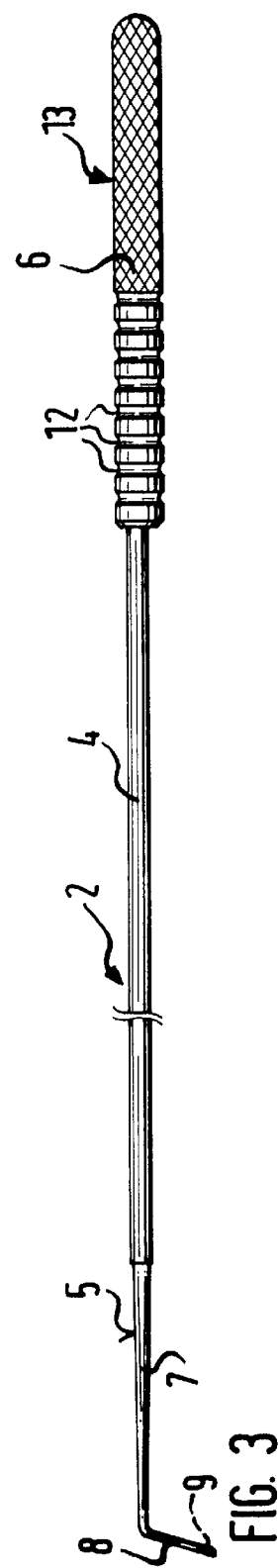
FIG. 3 a rear view of the constructional unit according to FIG. 2.

In FIGS. 2 and 3 the thread receiver on its own is shown. It can be recognised that this receiver comprises essentially of three parts, that is to say an elongate shank 4, which forms the middle part of the thread receiver, a needle insert 5 fastened to the distal end of the shank 4 and an elongate handle 6 fastened to the proximal end of the shank 4. The middle shank 4 is provided with a recess 4a extending along its whole length, said recess receiving the mentioned ligature thread. For this purpose the shank 4 may be comprised of solid material into which the recess 4a in the form of a groove having an adequately dimensioned cross section is incorporated. Alternatively, and as is shown for example by way of FIG. 2, which is the preferred embodiment form, the shank 4 may also be formed from a hollow shank, that is composed of a tube which for instance is provided with a longitudinal slit over its whole length, through which the ligature thread is inserted into the hollow shank. The whole hollow space and the longitudinal slit of the shank then form the recess 4a.

The needle insert 5 comprises a straight first needle section 7 connecting flush with the shank 4 and a second needle section 8 which is bent at an angle to said first needle section. The second section 8 comprises a designated, generally known form (not shown), e.g. a sickle shape, semicircular shape or likewise. Moreover the free end of the second needle section 8 is provided with the usual eye of the needle 9 through which the ligature thread 20 is pulled (FIG. 5). The first needle section 7 according to FIG. 2 is provided with a longitudinal groove 10 which extends over a part length of this needle section and graduates flushly into the distal end of the recess 4a or into the inside of the hollow shank 4.

The handle 6 which connects flush with the proximal end of the hollow shank 4 comprises an elongate component and is provided with a receiving groove 11 extending in the longitudinal direction of the handle, said receiving groove receiving the ligature thread 20 which proximally emerges from the hollow shank 4 (FIG. 5). The receiving groove 11 is flush with the recess 4a of the shank 4 and extends, as is shown, over the whole length of the handle 6. However it is possible that this groove only extends over a part length of the handle 6 connecting to the shank 4.

The handle 6 is provided with a structure 12, 13 on its surface for a better gripping and handling of the ligature instrument 1. This structure may for instance be composed of a multitude of shallow grooves 12 at a distance from one another. These grooves may provided over the whole length of the handle 6. Alternatively it may also be provided that the structure comprises a knurling or diamond knurl 13 which likewise may extend over the whole length of the handle 6. It may also be the case that both structure designs are provided, as is shown in FIG. 3. It can be recognised that on the shank side, the handle first connects to the grooved structure 12 which then follows the knurling or diamond knurl 13. In a further alternative design, with regard to the structure, it may be proceded to provide the circumferential grooves 12, which are at a distance from one another, over the whole length of the handle 6 and to knurl or diamond knurl the distances between the circumferential grooves. Knurling is also understood to include axial and circumferential knurling.

In FIG. 4 the second constructional unit 13 is shown on its own. It comprises a hollow outer shank 14 which has essentially the same length as the shank 4 of the thread receiver. This outer shank is provided with a continuous longitudinal slit 15. This longitudinal slit runs parallel to the recess 4a or to the longitudinal slit of the previously mentioned shank 4 of the thread receiver in order to be able to insert a ligature thread in the thread receiver. The insertion position of the outer shank 14 can be best seen from FIG. 6, in which both the longitudinal slits 4a and 15 are flush with each other.

The hollow outer shank 14 is provided at its proximal end with a slotted adjusting ring 16 which is rigidly attached to said outer shank (FIGS. 1, 4, 5, and 6) in order to be able to twist the outer shank 14 from the insertion position according to FIG. 6 into an overlapping position and position said shank in the overlapping position in which the slit 4a of the internally lying shank 4 is covered, so that a ligature thread inserted into the shank 4 does not move out through the longitudinal slit 4a of this shank.

For securing both previously mentioned positions of the outer shank 14 which surrounds the inner shank 4, the adjusting ring 16 comprises a latching device 17. This comprises a spring tensioned latching ball 18, which latches into latching notches 19 of the inner shank 4 and thus secures both mentioned positions of the hollow outer shank 14. Although it is advantageous to provide two latching notches 19 in the inner shank 4, one latching notch 19 only may be provided. Then, that notch which would ensure a secure overlapping of the recess 4a or the longitudinal slit of the inner shank 4 by the outer shank 14 would be chosen.

The embodiment example according to FIG. 7 differs from that according to FIG. 1 in that the outer shank 14 is shorter than the inner shank 4. The outer shank begins distally together with the inner shank and ends at a desired distance A in front of the handle 6. However, the recess 4a or a correspondiing slit of the inner shank projects proximally from the outer shank 14 including the adjusting ring 16 and may likewise end at a certain distance in front of the handle 6, as can be deduced from FIG. 7. With this embodiment it is not necessary that the handle 6 comprises a slit or a recess which allows a lateral exit of the ligature thread 20 or another flexible or bendable assisting device, such as for example a catheter or a stent.

FIG. 8a represents a further design possibility for the recess 4a of the inner shank 4. If this shank is comprised of tube material, a circumferential section in the form of a channel may be incorporated in the tube wall receding into the inside of the tube. The channel then receives the ligature thread 20. Whilst FIG. 8a shows the unclosed channel 4a, this is closed in FIG. 8b by twisting the outer shank 14 about 90°, said outer shank with part of its wall overlapping the channel and thus securing the ligature thread in the channel.

FIG. 8c shows an inner shank 4 which additionally to the recess 4a, comprises a second recess 4b which for instance lies diametrically opposite the first recess. If the shank 4 is composed of a tube material, this second recess 4b is likewise incorporated receding into the tube wall of this shank. If the shank 4 is comprised of solid material, the second recess 4b is formed by machining e.g. by milling. A catheter 21 for example, which is to be positioned in the body of a patient may be inserted into the second recess. It is also possible to provide more than two recesses in the shank.

For overlapping the recesses 4a, 4b using the outer shank 14, this outer shank is twisted about the inner shank 4, this being firstly over the first recess 4a and then after insertion of the additional assisting means 21, over the second recess 4b. With regard to its position in FIG. 8c, the outer shank is then twisted about 270° in order to secure all assisting devices in their recesses.

FIG. 8d shows essentially the embodiment according to FIG. 8c with the exception that the outer shank 14 comprises two slits 15, 15b, so that each recess 4a, 4b is allocated to an insertion slit. While the one slit 14 preferally extends over the whole length of the shank 15, this is not the case with the other slit 15b. This slit extends roughly over half the shank length in order to ensure an adequate shank stability.

FIG. 9 shows a further embodiment of the inner shank 4 when this shank is composed of a tube material. Within the tube cross section an additional lumen 22, formed by a tube, may be provided and through which an endoscope optic (not shown) as an additional assisting device may be guided. Such an optic which is introduced into the instrument at the proximal side at a suitable location, simplifies the handling of the ligature thread or likewise in the body of the patient and does away with the need to make a second puncture in the body of the patient.

Instead of the more previously described adjusting ring 16 for the twist adjusting of the outer shank 14 about the inner shank 4, a threaded connection between both the shanks may also be provided. FIG. 9 shows such a connection. For this purpose the outer shank 14 is provided with an internal thread 23 at its proximal end region, said thread engaging with an external thread 24 of the inner shank 4, said external thread extending over an appropriate region of the inner shank. The thread 23, 24 is so formed that the frictional engagement between the thread turns is sufficient to hold the outer shank, with regard to the recess 4a or recesses, in each case in its open position as well as also in its closed position.

In a further formation of the endoscopic instrument the outer shank is designed separable from the inner shank 4, so that it may be pulled from this in the distal direction. As can be understood without further ado, the latching of the adjusting ring 16 as well as the thread connection 23, 24 permits a simple releasing of the shanks from one another. The slit 15 of the shank 14 has an appropriate width so that the needle bend 8 can pass the slit.

In FIGS. 10, 11, and 12 there is shown a second embodiment example of the endoscopic instrument 1 which is equipped with addition devices. The inner shank 4 manufactured from tube material is, apart from the already mentioned additional lumen 22 for an endoscope optic (not shown), provided in its inside with two further lumens 25 and 26 consisting of tubes, these lumens running through the shank 4 as flushing lumens. For this purpose the handle 6 comprises two laterally distanced connections 27 and 28 as well as an optic lumen 22b. Thus flushing liguid may run through the instrument 1 via the connection 27 to the location of operation and may again be suctioned out of the operation location via the connection 28. Otherwise the inner shank 4 comprises the previously described recess 4a in which the catheter is inserted (FIG. 11). When the catheter 21 has been inserted into the recess 4a the outer shank 14 is twisted about 90°, this being for example with the aid of the adjusting ring 16, so that the recess 4a is covered and the section of the catheter 21 located in this recess is secured against accidental dislocation out of the recess.

The embodiment form according to FIG. 12 differs from that according to FIG. 11 in that lumens 22, 25 and 26 of the inner shank 4 are not formed by additional tubes, but with regard to the cross section are formed by a particular wall contour of the inner shank 4. It can be recognised that the lumen 22 for an endoscope optic which can be passed through is formed by a channel-type arching 22a of the tube material of the shank 4. The apex of the arching 22a at the same time lies adjacent the apex of the recess 4a which receives the catheter 21. Space for the endoscope optic (not shown) is thereby created between the arching 22a and the outer shank 14. By way of the recess 4a and the arching 22a, which lie adjacent each other at their apexes, simultaneously, both flushing lumens 25 and 26 are formed in the inner shank 4. These flushing lumens are also connected to the connections 27 and 28. Otherwise the functional manner of this embodiment example corresponds to that of the first embodiment example.

In FIG. 13 and 14 there is shown a third embodiment example of the endoscopic instrument. This embodiment example differs from that according to FIGS. 10 and 11 in that instead of a lumen 22 for an endoscope optic which can be passed through, a second recess 4b is provided in the inner shank 4 in the already previously described design, and in that the outer shank 14 is equipped with a second insertion slit 15a for the second recess 4b. Whilst in the one recess 4a a catheter 21 may be inserted, a ligature thread 20 or other assisting device may be located in the other recess 4b. When both these assisting devices are inserted into the inner shank, the outer shaft 14, on operation of the adjusting ring 16, is twisted about approx. 90° so that both recesses are covered by the outer shank 14 and secured therein. The slit design in the outer shank 14 can be such that both slits 15, 15a extend only over part of the length of the shank in order to ensure the stability of the outer shank. It is however possible that one of the slits 15, 15a also may extend over the whole length of the outer shank 14; this is shown dashed in FIG. 13.

The complete or part covering of an assisiting device using the outer shank 14 such as a catheter inserted into the recess 4a of the inner shank 4, or with several recesses of a corresponding number of assisting devices, may be effected by the distal displacement of the outer shank should one or the slits 15 only extend over a part length of the outer shank, as is shown in FIG. 13. Depending on how far axially a catheter is inserted into the corresponding recess 4a, the remaining part length, i.e. the unslotted part length of the outer shank 14 may be sufficient to cover the catheter. For this the pulled back outer shank is displaced so far distally after the insertion of the catheter or likewise, that the recess 4a of the inner shank 4 and thus the catheter is covered by the outer shank 14 in this region, which is clear to the man skilled in the art in connection with FIG. 13. A positioning of the outer shank in its distal overlapping position may be effected by the latching device 17 of the adjusting ring 16. For this the inner shank 4 may comprise a latching notch (not shown) at a suitable location so that the outer shank is secured in a kept position.

The embodiment examples according to FIGS. 10 and 13 are applicable without a needle insert, so this is not shown. If it is necessary, a needle insert may be however mounted to the distal end of these instruments. Mainly the instrument according to the examples 10 to 14 are applied for inserting catheters.

What is claimed is:

1. An endoscopic instrument for introducing at least one elongate medical assisting device into the body of a patient, comprising:

an elongate hollow tubular inner shank having a proximal end and a distal end, having an axially aligned elongate handle at its proximal end, and having at least one longitudinal recess formed as a channel for receiving and guiding an elongate medical assisting device, said recess beginning at said distal end and extending at least partly towards said proximal end; and a hollow elongate outer shank, mounted for rotation about said inner shank so as to concentrically enclose at least a part of said inner shank, having a proximal end and a distal end, an inner wall, and having at least one longitudinal slit extending from its distal end at least partly towards its proximal end, wherein:

when said outer shank is axially rotated about said inner shank to a first position, said longitudinal slit is aligned with said recess, such that an elongate medical assisting device may be readily introduced into said recess, and when said outer shank is axially rotated about said inner shank to a second position, said recess is thereby overlapped by said inner wall of said outer shank, such that said elongate medical assisting device is retained within said recess by said inner wall.

2. The endoscopic instrument of claim 1, wherein said inner shank comprises at least one additional axially aligned tubular lumen for guiding and receiving an additional elongate medical assisting device.

3. The endoscopic instrument of claim 1, wherein said inner shank further comprises at least one notch radially disposed around its proximal end, and wherein said outer shank further comprises a slotted adjusting ring attached at said proximal end of said outer shank, and axially aligned with said outer shank, said adjusting ring having an inner wall in contact with said at least one notch of said inner shank, said adjusting ring further comprising a latching device, disposed on said adjusting ring inner wall, operable to releasably engage at least one said notch when said outer shank is rotated about said inner shank, such that said outer shank may thereby be retained in one of said first and said second positions.

4. The endoscopic instrument of claim 1, wherein said outer shank further comprises an internal thread extending along at least a part of its length from its proximal end, and wherein said inner shank further comprises an external thread, extending along at least a part of its length from its proximal end, for rotably engaging said inner thread.

5. The endoscopic instrument of claim 1, wherein said outer shank is releasably mounted about said inner shank.

6. The endoscopic instrument of claim 1, wherein said handle comprises a longitudinal receiving groove for receiving an elongated medical assisting device, extending from said second end to said first end, said receiving groove being axially aligned with said recess of said inner shank.

7. The endoscopic instrument of claim 6, wherein said handle further comprises an outer covering for enabling improved manipulation of said handle.

8. The endoscopic instrument of claim 7, wherein said outer covering comprises at least one of a plurality of circumferential grooves disposed along said handle, and a knurling pattern covering an outer surface of said handle.

9. The endoscopic instrument of claim 6, wherein said inner shank further comprises a first tubular lumen, extending from said proximal end of said inner shank to its distal end, for receiving flushing fluid and for delivering said flushing fluid into the body of the patient, a second tubular lumen, extending from said proximal end of said inner shank, to its distal end for suctioning fluid from the body of the patient, and a third tubular lumen extending from said proximal end of said inner shank to its distal end, and wherein said handle comprises:

a first tubular connection, angularly mounted along said handle, for communicating with said first lumen, a second tubular connection, angularly mounted along said handle, for communicating with said second lumen, and a third tubular connection longitudinally disposed within said handle for communicating with said third lumen.

10. The endoscopic instrument of claim 1, further comprising a needle insert, connected to said distal end of said inner shank, having a straight first needle section axially aligned and flush with said inner shank, a second needle section bent at a predetermined angle with respect to said first needle section, said second needle section comprising a needle eye.

11. The endoscopic instrument of claim 10, wherein said first needle section comprises a longitudinal groove aligned with said recess of said inner shank.

* * * * *